(12) United States Patent
Mattingly et al.

(10) Patent No.: US 11,833,228 B2
(45) Date of Patent: Dec. 5, 2023

(54) FLUORINATED BETA-HYDROXYBUTYRIC ACIDS FOR PET IMAGING

(71) Applicant: The Governors of the University of Alberta, Edmonton (CA)

(72) Inventors: Stephanie Mattingly, Louisville, KY (US); Frank Wuest, Edmonton (CA); Ralf Schirrmacher, Edmonton (CA); Melinda Wuest, Edmonton (CA); Eugene Fine, Bronx, NY (US)

(73) Assignee: The Governors Of The University Of Alberta (CA)

( * ) Notice: Subject to any disclaimer, the term of this patent is extended or adjusted under 35 U.S.C. 154(b) by 0 days.

(21) Appl. No.: 16/992,940

(22) Filed: Aug. 13, 2020

(65) Prior Publication Data

US 2021/0046196 A1 Feb. 18, 2021

Related U.S. Application Data

(60) Provisional application No. 62/886,463, filed on Aug. 14, 2019.

(51) Int. Cl.
| | | |
|---|---|---|
| *A61K 51/04* | (2006.01) | |
| *C07C 53/21* | (2006.01) | |
| *C07B 59/00* | (2006.01) | |
| *A61P 5/00* | (2006.01) | |

(52) U.S. Cl.
CPC ............ *A61K 51/0402* (2013.01); *A61P 5/00* (2018.01); *C07B 59/001* (2013.01); *C07C 53/21* (2013.01); *C07B 2200/05* (2013.01)

(58) Field of Classification Search
CPC ... A61K 51/0402; A61P 35/00; C07B 59/001; C07B 2200/05; C07C 53/21

USPC ......................................................... 424/1.89
See application file for complete search history.

(56) References Cited

U.S. PATENT DOCUMENTS

2013/0209580 A1* 8/2013 Russell ................ A61K 31/593
424/655

FOREIGN PATENT DOCUMENTS

| WO | WO-2015026944 A1 * | 2/2015 | .............. C12P 19/62 |
| WO | WO-2019183564 A1 * | 9/2019 | ............. A61K 31/19 |

OTHER PUBLICATIONS

Bouteldja et al. Metab. Clin. Exper. 63 (2014) 1375-1384. (Year: 2014).*
Graham et al. J. Am. Chem. Soc. 2014, 136, 5291-5294. (Year: 2014).*
Budin et al. Bioorg. Chem. 80 (2018) 560-564. (Year: 2018).*
Graham, Thomas J.A.; Lambert, R. Frederick; Ploessl, Karl; Kung, Hank F, and Doyle, Abigail G. Enantioselective Radiosynthesis of Positron Emission Tomography (PET) Tracers Containing [18F]Fluorohydrins. Journal of the American Chemical Society Apr. 9, 2014; 136(14):5291-5294.
Mattingly, Stephanie J.; Wuest, Frank; and Schirrmacher, Ralf. Synthesis of 2-Fluoroacetoacetic Acid and 4-Fluoro-3-hydroxybutyric Acid. Synthesis 2019; 51(11): 2351-2358.

* cited by examiner

*Primary Examiner* — Michael G. Hartley
*Assistant Examiner* — Sean R Donohue
(74) *Attorney, Agent, or Firm* — Kirsten M. Oates; Rodman & Rodman LLP (57) ABSTRACT

Beta-hydroxybutyric acid-based radiopharmaceuticals, pharmaceutical compositions comprising same, methods for preparing same, and methods of using same for diagnostic imaging and non-imaging tracer studies are provided.

13 Claims, 11 Drawing Sheets

(S)[¹⁸F]FBHB

FIG. 1A (R)[¹⁸F]FBHB

FIG. 1B

Reagents and conditions: (a) K[¹⁸F]F-K222, MeCN, 90 °C, 25 min; (b) KCN aq., MeCN, 90 °C, 15-20 min; (c) Nitrilase, recombinant, expressed in E. coli, aq. pH 9, 30 °C, 1-2h

FLUORINATED BETA-HYDROXYBUTYRIC ACIDS FOR PET IMAGING

CROSS-REFERENCE TO RELATED APPLICATION

This application claims the benefit of U.S. Provisional Patent Application Ser. No. 62/886,463, filed Aug. 14, 2019, the entirety of which is incorporated herein by reference.

FIELD OF THE INVENTION

The present invention relates to beta-hydroxybutyric acid-based radiopharmaceuticals, pharmaceutical compositions comprising same, methods for preparing same, and methods of using same for diagnostic imaging and non-imaging tracer studies.

BACKGROUND OF THE INVENTION

Positron emission tomography (PET) is a nuclear medicine imaging technique for studying metabolic and physiological processes and tissue microenvironments, and diagnosing or treating diseases including cancer, heart disease and brain abnormalities. PET uses non-toxic radiopharmaceutical agents formed from biologically relevant molecules labelled with positron-emitting radionuclides. Following administration to the body, the radiopharmaceutical agent localizes within the tissue of interest. When the isotope decays, it emits a positron which then annihilates with an electron of a nearby atom, producing gamma rays. The PET scanner detects gamma ray photons, thereby producing an image of the tissue for interpretation by a radiologist.

Due to its emission of positrons and half-life of 110 minutes, fluorine-18 ($^{18}F$) is the standard radionuclide for PET, and is commonly synthesized into fluorodeoxyglucose (FDG) to form 2-deoxy-[$^{18}F$] fluoro-D-glucose ($^{18}F$-FDG). FDG is a sugar compound which is processed by growing cancer cells, the brain, and cardiac muscles. Transport of sugar through cell membranes requires transport proteins known as GLUTs. Imaging tumors with PET traditionally uses [$^{18}F$]-FDG as the imaging agent to take advantage of the characteristic overexpression of facilitated hexose transporter isoform GLUT1 (SLC2A1) in certain cancer cells. [$^{18}F$]-FDG is subsequently trapped and accumulated within the cancer cells as a result of phosphorylation at the 6-position by hexokinase II, an enzyme which is overexpressed in many cancers. [$^{18}F$]-FDG has thus been used to evaluate metastatic and recurring cancer, and to detect primary disease.

However, [$^{18}F$]-FDG is ineffective in the detection of small tumors and more differentiated sub-types, and accumulates in areas of inflammation, making it difficult to distinguish between cancerous and inflamed tissues upon imaging. Macrophages and other immune cells have been implicated in the generation of false positives when using [$^{18}F$]-FDG due to increased uptake of large quantities of glucose and [$^{18}F$]-FDG by these cells. Further, PET imaging using [$^{18}F$]-FDG has limited application in certain tissues including heart and brain due to high background interference.

Further, the stages for PET imaging generally involve radionuclide production in a cyclotron, synthesis of a precursor, radiolabelling in a radiotracer laboratory, purification, administration to a subject, a PET scan, and image analysis and evaluation. PET chemistry with $^{18}F$ must be completed rapidly, preferably within an hour, to provide sufficient radioactive tracer for a PET scan. The preparation of imaging radiopharmaceuticals using $^{18}F$ as a PET radionuclide requires rapid high yield reactions which can be accomplished by the preparation of suitable precursor molecules. Preparation of suitable precursors can be difficult and time consuming.

As an alternative to [$^{18}F$]-FDG, 3-hydroxybutyric acids labelled with either $^{11}$carbon or $^{14}$carbon isotopes have been developed; however, the half-lives of such isotopes are not conducive to clinical studies since $^{11}$carbon has a brief half-life of only 20 minutes, while $^{14}$carbon has an overly lengthy half-life of 5,730 years. Further, the rapid metabolism of [$^{11}C$] D(–)-3-hydroxybutyrate and consequent loss of [$^{11}C$]$CO_2$ through respiration limits its usefulness as an investigative tool. Accordingly, there is a need for improved radiopharmaceuticals for PET imaging.

SUMMARY OF THE INVENTION

The present invention relates to beta-hydroxybutyric acid-based radiopharmaceuticals, pharmaceutical compositions comprising same, methods for preparing same, and methods of using same for diagnostic imaging and non-imaging tracer studies.

In one aspect, the invention comprises a radiopharmaceutical of the formula (I):

or a prodrug, pharmaceutically acceptable salt, metabolite, solvate, hydrate, or radioisotope thereof. In one embodiment, the radiopharmaceutical comprises (S)-[$^{18}F$]γ-fluoro-β-hydroxybutyric acid.

In another aspect, the invention comprises a radiopharmaceutical of the formula (II):

or a prodrug, pharmaceutically acceptable salt, metabolite, solvate, hydrate, or radioisotope thereof. In one embodiment, the radiopharmaceutical comprises (R)-[$^{18}F$]γ-fluoro-β-hydroxybutyric acid.

In another aspect, the invention comprises a method of forming a radiopharmaceutical comprising the steps of:

displacing a tosylate leaving group of (2S)-(–)-glycidyl tosylate or (2R)-(–)-glycidyl tosylate by nucleophilic [$^{18}F$] fluoride to form (S)-[$^{18}F$]epifluorohydrin or (R)-[$^{18}F$]epifluorohydrin;

adding potassium cyanide to produce gamma-[$^{18}F$]fluoro-beta-hydroxy nitrile, followed by purification; and converting the gamma-[$^{18}F$]fluoro-beta-hydroxy nitrile using nitrilase to form (S)-[$^{18}F$]γ-fluoro-β-hydroxybutyric acid or (R)-[$^{18}F$]γ-fluoro-β-hydroxybutyric acid.

In another aspect, the invention comprises a composition comprising any of the above radiopharmaceuticals and a pharmaceutically acceptable carrier.

In another aspect, the invention comprises a method for diagnosing, staging, or treating a disorder in a subject comprising:

administering a radiopharmaceutical to the subject; and imaging an organ or tissue of interest using positron emission tomography;

wherein the radiopharmaceutical comprises the compound of formula (I), formula (II), or a prodrug, pharmaceutically acceptable salt, metabolite, solvate, hydrate, radioisotope, or composition thereof, and is capable of being retained within the organ or tissue sufficient to emit positrons for detection by positron emission tomography.

In one embodiment, the method further comprises providing a suitable medical treatment to the subject for the disorder based on the results obtained from imaging the organ or tissue of interest using positron emission tomography.

In another aspect, the invention comprises a method for monitoring a disorder in a subject comprising:

administering a radiopharmaceutical to a subject undergoing medical treatment for the disorder;

imaging an organ or tissue of interest using positron emission tomography; and comparing the quantity or distribution of the radiopharmaceutical present in the subject with a control quantity or distribution indicative of the effectiveness of the medical treatment, wherein the radiopharmaceutical comprises the compound of formula (I), formula (II), a prodrug, pharmaceutically acceptable salt, metabolite, solvate, hydrate, radioisotope, or composition thereof, and is capable of being retained within the organ or tissue sufficient to emit positrons for detection by positron emission tomography.

In one embodiment, the disorder comprises a disease or condition that exhibits deviations or alterations from normal energy metabolism. In one embodiment, the disorder is selected from Alzheimer's disease, epilepsy, cancer, cardiovascular disease, or diabetes. In one embodiment, the cancer is breast cancer. In one embodiment, the cardiovascular disease is heart failure. In one embodiment, the organ or tissue is selected from the brain, breast, heart, eye, or a tumor. In one embodiment, the medical treatment is ketogenic diet therapy.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described by way of an exemplary embodiment with reference to the accompanying simplified, diagrammatic, not-to-scale drawings. In the drawings.

DETAILED DESCRIPTION OF PREFERRED EMBODIMENTS

Before the present invention is described in further detail, it is to be understood that the invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a," "an," and "the" include plural referents unless the context clearly dictates otherwise.

The present invention relates to beta-hydroxybutyric acid-based radiopharmaceuticals, pharmaceutical compositions comprising same, methods for preparing same, and methods of using same for diagnostic imaging and non-imaging tracer studies.

As used herein, the term "beta-hydroxybutyric acid-based" means a radiopharmaceutical which includes beta-hydroxybutyric acid, analogs or derivatives thereof. As used herein, the term "beta-hydroxybutyric acid" refers to a beta hydroxyl acid having the chemical formula $CH_3CH(OH)CH_2CO_2H$. Beta-hydroxybutyric acid is a chiral compound with two enantiomers: D-β-hydroxybutyric acid and L-β-hydroxybutyric acid.

Figure 1A:
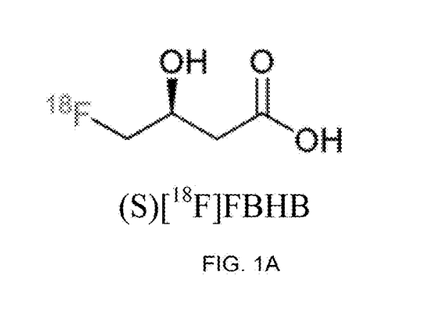
FIG. 1A shows the chemical structure of the radiopharmaceutical (S)-[$^{18}$F]γ-fluoro-β-hydroxybutyric acid ("(S) [$^{18}$F]FBHB").
Figure 1B:
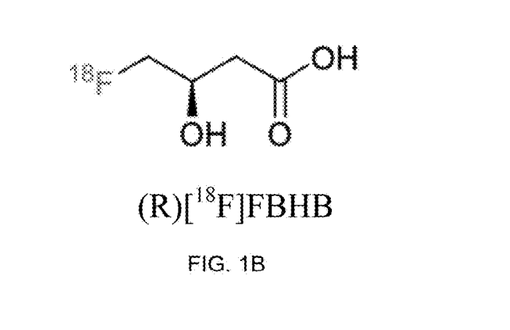
FIG. 1B shows the chemical structure of the radiopharmaceutical (R)-[$^{18}$F]γ-fluoro-β-hydroxybutyric acid ("(R) [$^{18}$F]FBHB").

When designing the beta-hydroxybutyric acid-based radiopharmaceuticals, the compounds were made to differ with respect to the absolute stereochemistry of the hydroxylated carbon, and were designed to serve as radiofluorinated analogues of endogenous non-fluorinated metabolites. Exemplary beta-hydroxybutyric acid-based radiopharmaceuticals of the invention are shown in FIGS. 1A and B. In one embodiment shown in FIG. 1A, the beta-hydroxybutyric acid-based radiopharmaceutical comprises the compound of formula (I):

(I)

or a prodrug, pharmaceutically acceptable salt, metabolite, solvate, hydrate, or radioisotope thereof.

In one embodiment, the beta-hydroxybutyric acid-based radiopharmaceutical comprises (S)-[$^{18}$F]γ-fluoro-β-hydroxybutyric acid. The native metabolite, D(−)-3-hydroxybutyrate is known as a ketone body. As used herein, the term "ketone body" refers two related compounds (acetoacetic acid and beta-hydroxybutyric acid) produced by the liver from fatty acids during periods of fasting or carbohydrate restrictive diets. D(−)-3-hydroxybutyrate serves as the primary fuel (supplanting glucose) of the heart, brain, and skeletal muscle in mammals under prolonged dietary fasting conditions or carbohydrate restriction, and is the central metabolite of fat metabolism (as glucose is for carbohydrate metabolism).

In one embodiment shown in FIG. 1B, the beta-hydroxybutyric acid-based radiopharmaceutical comprises the compound of formula (II):

(II)

or a prodrug, pharmaceutically acceptable salt, metabolite, solvate, hydrate, or radioisotope thereof.

In one embodiment, the beta-hydroxybutyric acid-based radiopharmaceutical comprises (R)-[$^{18}$F]γ-fluoro-β-hydroxybutyric acid. The native metabolite L(+)-3-hydroxybutyrate is of unknown origin with unknown metabolism but theorized to be produced by heart cells and shunted to the nervous system and brain into lipid and sterol synthesis pathways.

Figure 2:
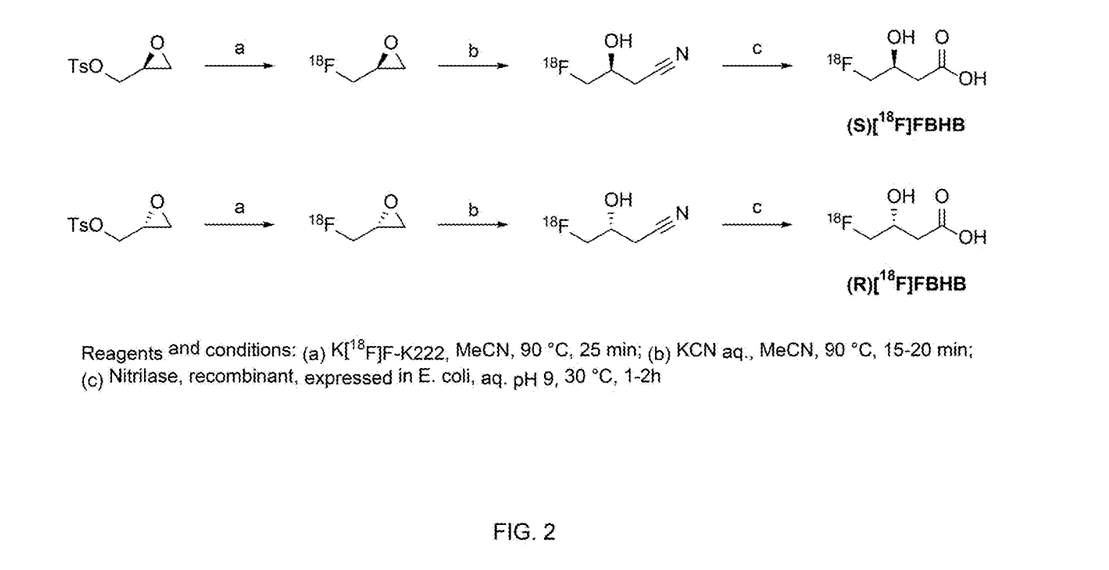
FIG. 2 shows a synthetic scheme for producing the radiopharmaceuticals of FIGS. 1A-B.

In one aspect, the present invention is directed to processes for preparing radiopharmaceuticals. In one embodiment, the compound of formula (I) is prepared using (2S)-(−)-glycidyl tosylate as a starting material. In one embodiment, the compound of formula (II) is prepared using (2R)-(+)-glycidyl tosylate as a starting material. Both starting materials are inexpensive and commercially available. In one embodiment, the process for preparing each radiopharmaceutical comprises a three step synthesis. In one embodiment shown in FIG. 2, the compound of formula (I) is prepared beginning with (2S)-(−)-glycidyl tosylate. The first step of the synthesis is the formation of (S)-[$^{18}$F]epifluorohydrin via displacement of the tosylate leaving group by nucleophilic [$^{18}$F]fluoride. The second step is the direct addition (without intervening purification) of potassium cyanide and the consequent ring opening of the epoxide moiety by the cyanide anion. This produces an intermediate product, a gamma-[$^{18}$F]fluoro-beta-hydroxy nitrile, which can be purified either by reverse phase HPLC or by solid phase extraction cartridges. Finally, the intermediate nitrile is converted to the final product acid through an enzymatic reaction using nitrilase (commercially available, recombinant, expressed in *E. coli*). The purification of the final product acid is accomplished through an ion exchange cartridge. The synthesis of the isomer II is accomplished in the same way with the exception of starting with (2R)-(+)-glycidyl tosylate.

In contrast, the conventional process for preparing a radiopharmaceutical typically involves radionuclide production in a cyclotron, synthesis of a precursor, radiolabelling in a radiotracer laboratory, and purification. However, the process for preparing the radiopharmaceuticals of the present invention does not require the step of synthesizing a precursor. It is thus contemplated that any facility equipped for radiofluorination may readily produce the radiopharmaceuticals of the present invention without undue preparation beyond the purchase of inexpensive, commercially available starting materials.

The utility of the radiopharmaceuticals may be confirmed by testing in various ways, including for example, in vitro cell culture assays using human cancer cells including, but not limited to, the MCF-7 and MDA-MB-231 breast cancer cell lines which are responsive to the radiopharmaceuticals. The radiopharmaceuticals may also be evaluated in vivo using murine models. For example, the radiopharmaceuticals may be administered to mice having tumors by various routes of administration including, but not limited to, orally, intravenously or intraperitoneally in appropriate dosage forms and fixed dosages. Assessments following treatment of the radiopharmaceuticals may include, but are not limited to, pharmacokinetics, biodistribution, uptake, cancer cell responses, toxicity, histopathology, and host morbidity. Uptake or retention may be assessed, as described for example, in Examples 1-7.

In one aspect, the invention comprises pharmaceutical compositions comprising the radiopharmaceuticals of the present invention in combination with one or more pharmaceutically acceptable carriers. Those skilled in the art are familiar with any pharmaceutically acceptable carrier that would be useful in this regard, and therefore the procedure for making pharmaceutical compositions in accordance with the invention will not be discussed in detail. Suitably, the pharmaceutical compositions may be in the form of liquids and solutions suitable for intravenous injection in liquid dosage forms as appropriate and in unit dosage forms suitable for easy administration of fixed dosages. The dosage of the radiopharmaceutical depends upon many factors that are well known to those skilled in the art, for example, the type and pharmacodynamic characteristics of the radiopharmaceutical; age, weight and general health condition of the subject; nature and extent of symptoms; any concurrent therapeutic treatments; frequency of treatment and the effect desired.

In one aspect, the invention comprises a method for diagnosing, staging, or treating a disorder in a subject comprising: administering a radiopharmaceutical to the subject; and imaging an organ or tissue of interest using positron emission tomography; wherein the radiopharmaceutical is the compound of formula (I), (II), a prodrug, pharmaceutically acceptable salt, metabolite, solvate, hydrate, radioisotope, or composition thereof, and is capable of being retained within the organ or tissue sufficient to emit positrons for detection by positron emission tomography.

In one embodiment, the method further comprises providing a suitable medical treatment to the subject for the disorder based on the results obtained from imaging the organ or tissue of interest using positron emission tomography. The subject may then be provided with a medical treatment or management program to treat, ameliorate, or prevent the progression of the disorder. As used herein, the term "medical treatment" or "management program" refers to an effective treatment modality or program to include pharmacologic and non-pharmacologic components for treating, ameliorating, and/or preventing the disorder. As used herein, the terms "treatment," "treating," "treat," and the like, refer to obtaining a desired pharmacologic and/or physiologic effect. The effect can be prophylactic in terms of completely or partially preventing the disorder or symptoms thereof and/or can be therapeutic in terms of a partial or complete cure for the disorder and/or adverse effect attributable to the disorder. "Treatment" covers any treatment of a disorder in a subject, particularly in a human, and includes: (a) preventing the disorder in a subject which may be predisposed to the disorder but has not yet been diagnosed as having it; (b) inhibiting the disorder, i.e., arresting its development; and (c) relieving the disorder, i.e., causing regression of the disorder and/or relieving one or more symptoms of the disorder. "Treatment" can also encompass delivery of an agent or administration of a therapy in order to provide for a pharmacologic effect.

In one aspect, the invention comprises a method for monitoring (e.g., detecting positive metabolic changes in response to treatment) a disorder in a subject comprising: administering a radiopharmaceutical to a subject undergoing medical treatment for the disorder; imaging an organ or tissue of interest using positron emission tomography; and comparing the quantity or distribution of the radiopharmaceutical present in the subject with a control quantity or distribution indicative of the effectiveness of the medical treatment; wherein the radiopharmaceutical is the compound of formula (I), formula (II), a prodrug, pharmaceutically acceptable salt, metabolite, solvate, hydrate, radioisotope, or composition thereof, and is capable of being retained within the organ or tissue sufficient to emit positrons for detection by positron emission tomography.

As used herein, the term "disorder" refers to a disease or condition that exhibits deviations or alterations from normal energy metabolism. In one embodiment, the disorder is selected from Alzheimer's disease, epilepsy, cancer, cardiovascular disease, or diabetes. In one embodiment, the cancer is breast cancer. In one embodiment, the cardiovascular disease is heart failure. In one embodiment, the organ or tissue is selected from the brain, breast, heart, eye, or a tumor.

As used herein, the term "subject" means a human or other mammalian subject. Non-human subjects may include primates, livestock animals (e.g., sheep, cows, horses, goats, pigs) domestic companion animals (e.g., cats, dogs) laboratory test animals (e.g., mice, rats, guinea pigs, rabbits) or captive wild animals.

In the development of the present invention, it was found that the radiopharmaceuticals enabled PET imaging of tissue-specific uptake patterns that likely reflect those of their non-fluorinated endogenous counterparts and thus may provide information on deviations or alterations from normal energy metabolism in various disorders. As described in Examples 1-7, the beta-hydroxybutyric acid-based radiopharmaceuticals have been applied to PET imaging in normal BALB/C mice, tumor-bearing mice (breast cancer lines) under varying nutritional states, and murine models of heart failure.

FDG uptake is indicative of glucose uptake and more generally, carbohydrate metabolism, whereas uptake for example, of (S)[$^{18}$F]FBHB, is likely reflective of ketone body uptake and metabolism. To date, there is no clinically relevant radiotracer available which is applicable to the study of the metabolic state of ketosis (systemic fat mobilization) by PET imaging. The cell surface monocarboxylate transporters associated with ketone body uptake from circulation are distinct from glucose transporters and are upregulated in many cancers. Uptake of (S)[$^{18}$F]FBHB may be a marker of malignant tissue. In preliminary studies of mouse tumor models, xenograft tumors were visible by PET imaging after intravenous administration of (S)[$^{18}$F]FBHB (FIGS. 8A-B and 9A-C). Ketogenic diets have been used clinically in the treatment of epilepsy and diabetes. Ketogenic diets may also be used in cancer therapy, often as an adjunct to standard care. In one embodiment, the medical treatment which the subject may be undergoing is ketogenic diet therapy. In one embodiment, (S)[$^{18}$F]FBHB may be a useful tool for studying the clinical use of the ketogenic diet and as a screening tool to identify those patients most likely to respond to ketogenic diet therapy. When ketogenic diet therapy is applied, (S)[$^{18}$F]FBHB may further be used for treatment monitoring over the course of the diet therapy.

Figure 4A:
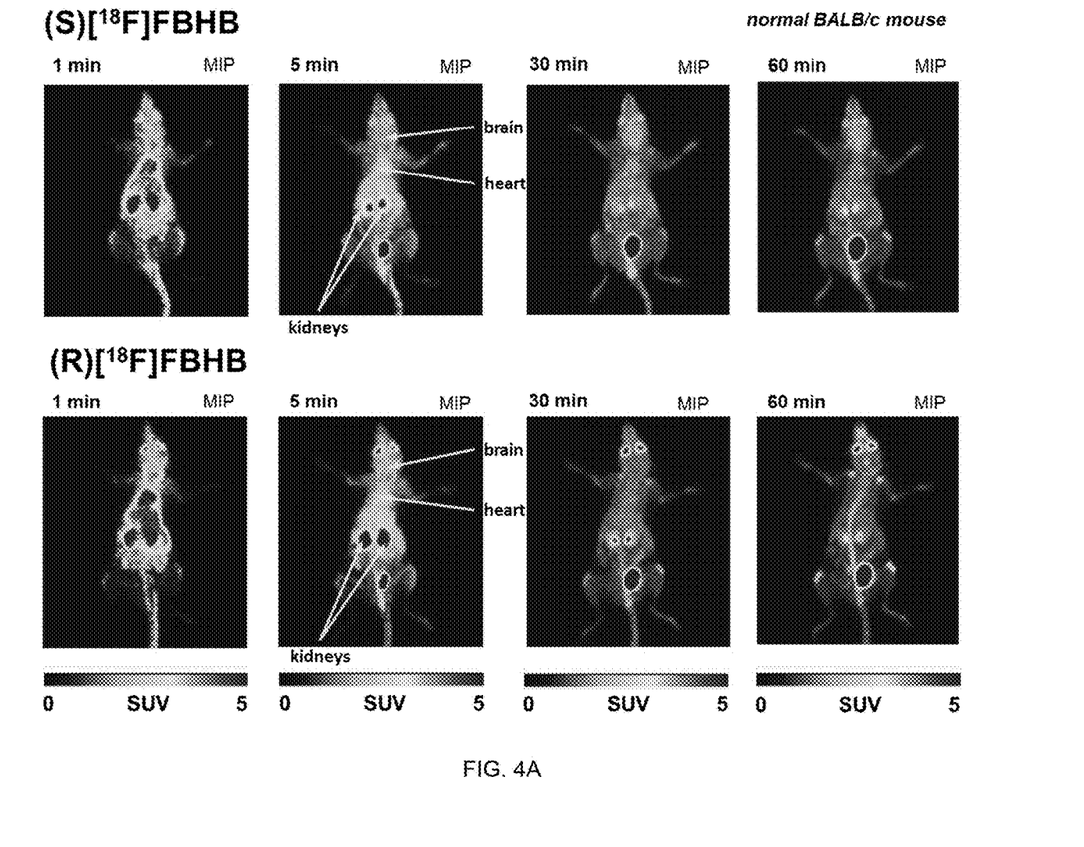
FIG. 4A shows dynamic PET scans over 30 minutes of normal BALB/c mice showing the anticipated renal clearance pathway for (S)[$^{18}$F]FBHB and (R)[$^{18}$F]FBHB (upper panel), and moderate heart and brain uptake and retention for both radiopharmaceuticals (lower panel). MIP, maximum intensity projection.
Figure 4B:
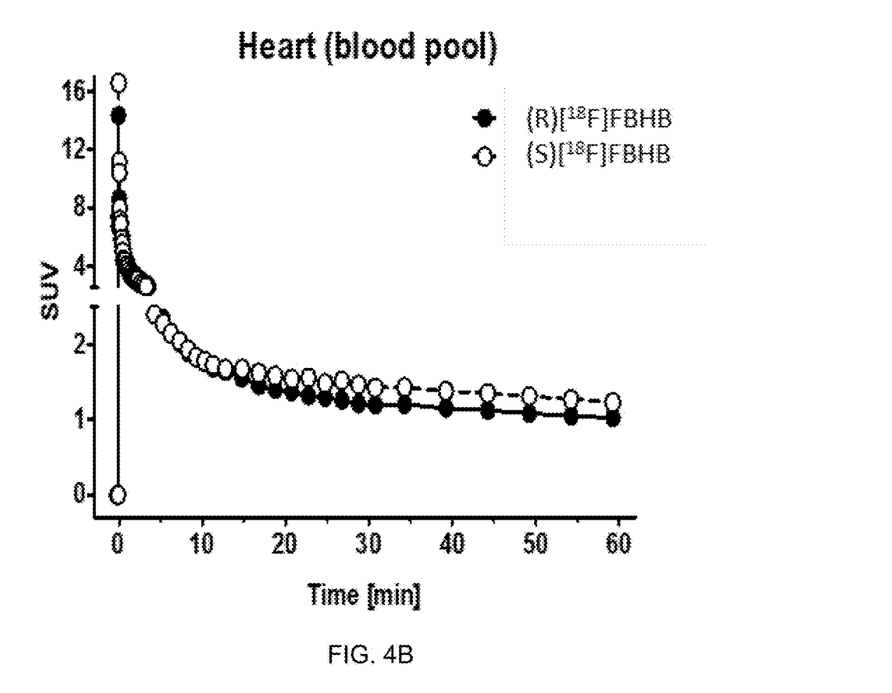
FIGS. 4B and 4C are graphs demonstrating moderate heart (FIG. 4B) and brain (FIG. 4C) uptake and retention for both (S)[$^{18}$F]FBHB and (R)[$^{18}$F]FBHB.
Figure 4C:
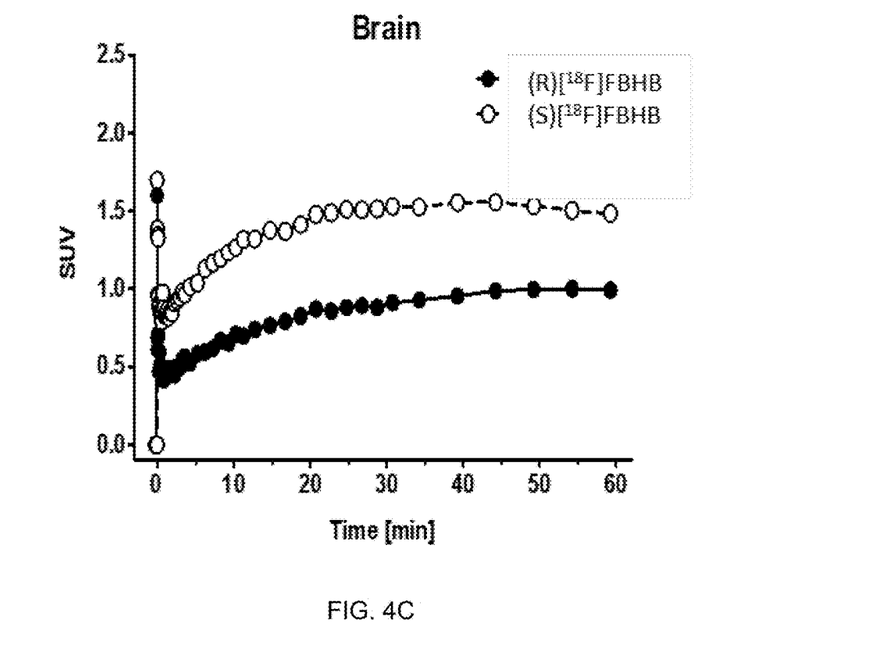

The radiopharmaceuticals display a moderate uptake in brain and heart which may allow for better imaging of brain and heart conditions. Initial PET images of the radiopharmaceuticals in normal BALB/C mice shows prolonged uptake in heart and brain, which are tissues difficult to visualize by [$^{18}$F]-FDG-PET (FIGS. 4A-C). The radiopharmaceuticals follow a renal clearance pathway.

Figure 5:
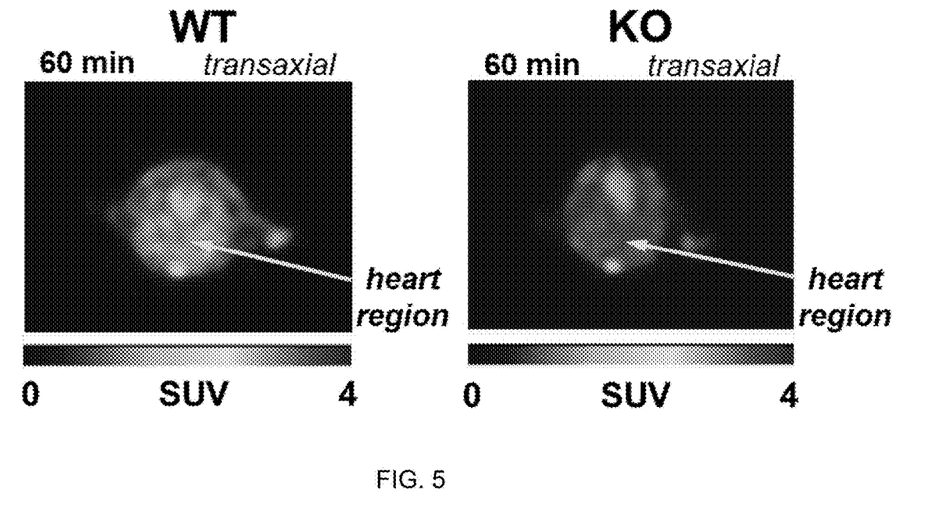
FIG. 5 shows transaxial PET scans using (R)[$^{18}$F]FBHB of the heart region of a wild type mouse with transverse aortic constriction-induced heart failure (left), and a mouse with induced heart failure and a knock out for the gene OXTC1 which codes for the ketone body metabolizing enzyme 3-oxoacid CoA transferase 1 (right).

In preliminary studies of heart failure mouse models with (R)[$^{18}$F]FBHB, PET images of the heart region in control mice appear distinct from heart failure models (FIG. 5).

Figure 6A:
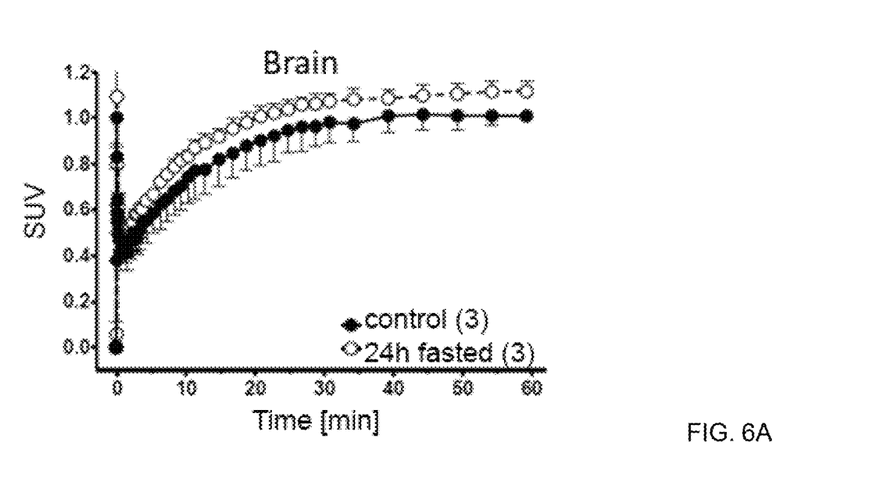
FIGS. 6A-C are graphs showing the dynamic uptake of (R)[$^{18}$F]FBHB expressed as SUV ratio versus time and indicating that a 24 hour fast of MCF7 tumor-bearing mice leads to increased heart (FIG. 6B) and brain (FIG. 6A) uptake of (R)[$^{18}$F]FBHB as well as better tumor retention (FIG. 6C).
Figure 6B:
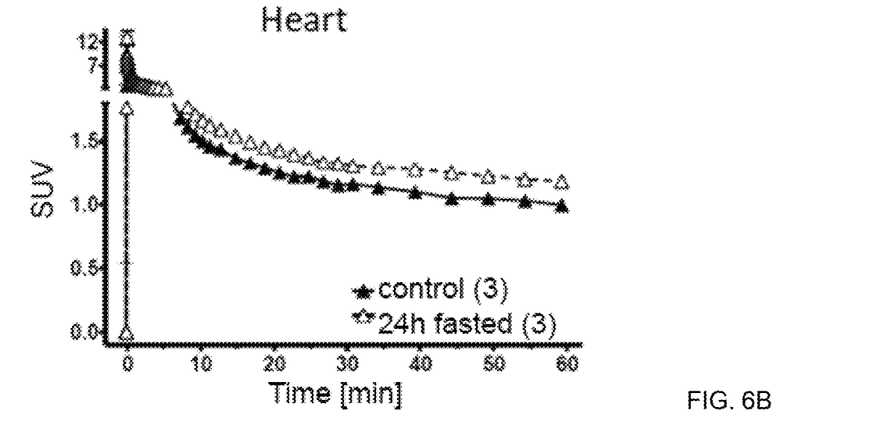
Figure 6C:
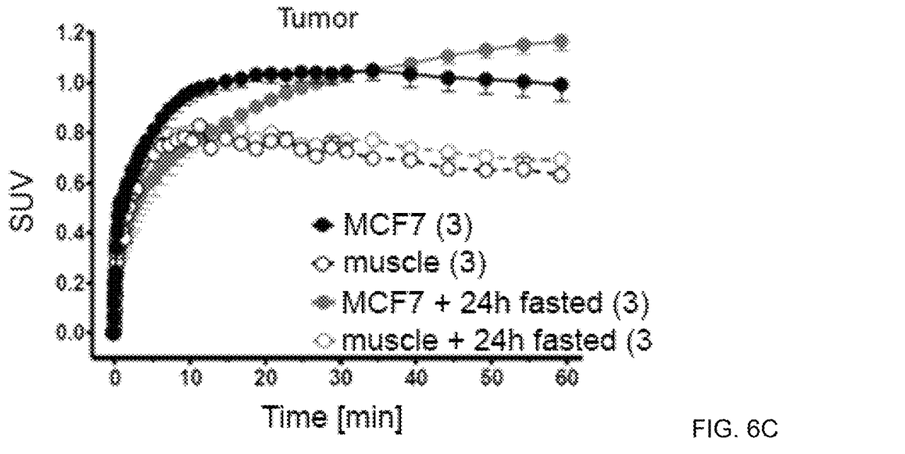

It was assessed whether the uptake of (R)[$^{18}$F]FBHB may be tunable using dietary adjustments. PET images of a 24-hour fasted tumor-bearing mouse were acquired and compared to a fed tumor-bearing mouse (FIGS. 6A-C). Indeed, radiopharmaceutical uptake in the brain and heart was higher in the fasted mouse as was retention of the radiopharmaceutical in the subcutaneous MCF-7 breast cancer tumor. As the metabolism of L(+)-3-hydroxybutyrate is not known, the radiotracer (R)[$^{18}$F]FBHB may be a useful tool for ascertaining its tissue of origin and metabolic fate.

Figure 7:
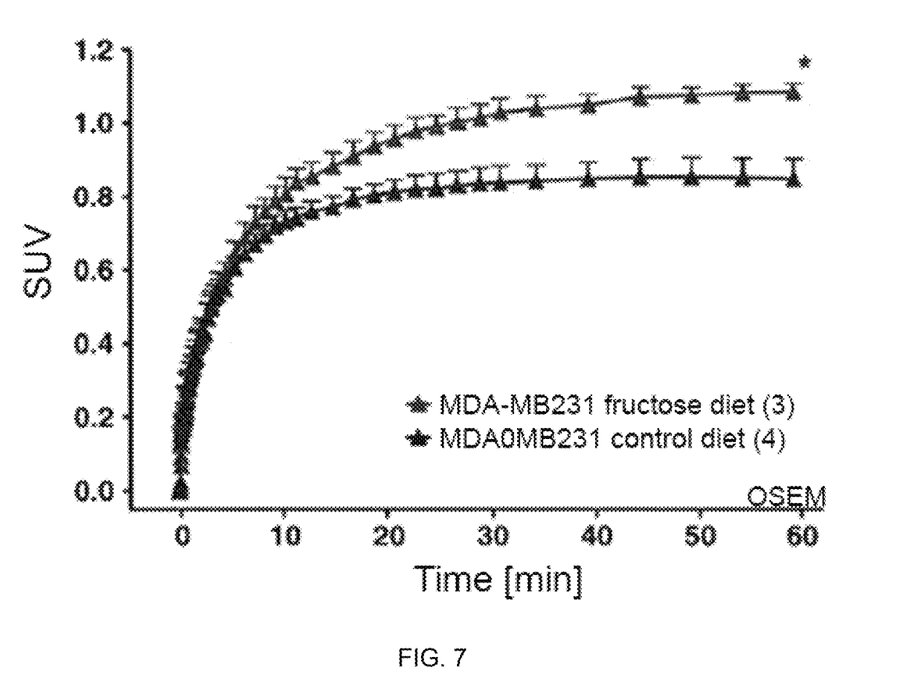
FIG. 7 is a graph showing the dynamic uptake of (R)[$^{18}$F] FBHB expressed as SUV ratio versus time and indicating that tumor retention of (R)[$^{18}$F]FBHB in mice bearing triple negative (MDA-MB231) breast cancer tumors was higher in mice fed a glucose-free, fructose-based diet.

Tumor retention of (R)[$^{18}$F]FBHB in mice bearing breast cancer tumors was higher in mice fed a glucose-free, fructose-based diet (FIG. 7). This clear impact of nutritional status on radiopharmaceutical uptake is indicative that (R)[$^{18}$F]FBHB is a metabolic tracer.

Embodiments of the present invention are described in the following Examples, which are set forth to aid in the understanding of the invention, and should not be construed to limit in any way the scope of the invention as defined in the claims which follow thereafter.

Example 1—Materials

Kryptofix® 222 (K222) (>98.0%) was purchased from TCI chemicals. Anhydrous CH$_3$CN (99.9+%, extra dry, acroseal) was purchased from Acros organics. All other chemicals and reagents were purchased from Millipore Sigma and used without further purification. Buffer pH was measured on a Fisher Scientific Accumet basic ab 15 pH meter. Thermoshaking was performed on an Eppendorf Thermomixer R. TLC plates were purchased from Millipore (TLC Silica gel 60 F254). RadioTLCs were read on a Bioscan AR-2000 plate reader.

Example 2—Animals and Treatments

Normal BALB/c mice or breast cancer xenografts were used for the PET imaging experiments. Human MDA-MB231 cells (3-5×10$^6$ cells in 100 µL PBS) were injected subcutaneously into 8-12 weeks old anesthetized female NIH-III nude mice (Charles River, Saint-Constant, QC, Canada). Tumors were grown for 3-4 weeks, reaching sizes of 300-500 mm$^3$. For fasting experiments, the food was removed from the mice for 24 h prior to the PET experiment.

Mice were anesthetized with isoflurane (40% O$_2$/60% N$_2$) and their body temperature was kept constant at 37° C. They were positioned and immobilized in prone position into the centre of the field of view of an INVEON® PET scanner (Siemens Preclinical Solutions, Knoxville, TN, USA). A transmission scan for attenuation correction was not acquired. Radioactivity present in the injection solution (0.5 mL insulin syringe) was determined using a dose calibrator (Atomlab™ 300, Biodex Medical Systems, New York, NY, USA). After the emission scan was started, radioactivity (4-8 MBq in 100-150 µL saline) was injected with a delay of ~15 s through a tail vein catheter. Dynamic PET data acquisition was performed in 3D list mode for 60 min. Dynamic list mode data were sorted into sinograms with 54 time frames (10×2 s, 8×5 s, 6×10 s, 6×20 s, 8×60 s, 10×120 s, 5×300 s).

Frames were reconstructed using the maximum a posteriori (MAP) reconstruction mode. No correction for partial volume effects was performed. Image files were further processed using the ROVER v2.0.51 software (ABX GmbH, Radeberg, Germany). Masks defining 3D ROI were set and defined by 50% thresholding. Mean standardized uptake values [SUV=(activity/mL tissue)/(injected activity/body weight) were calculated for each ROI. Time-activity curves (TAC) were generated from the dynamic scans using Graph-Pad® Prism 5.04 (GraphPad Software, La Jolla, CA, USA).

All semi-quantified PET data are expressed as means±SEM. Where applicable, statistical differences were tested by unpaired Student's t test and were considered significant for $p<0.05$ (*), $p<0.01$ () and $p<0.001$ (*).

Example 3—Determination of Blood Glucose and Ketone Concentrations in Mice

Blood samples from the same MDA-MB231 bearing nude mice as used for the PET experiments (unfasted and after 24 h fasting) were collected through tail vein puncture of the anesthetized mice. Blood drops were loaded onto test strips for glucose and ketone monitoring and concentrations were measured using a Freestyle Precision Neo® reading meter (Abbot Diabetes Care Ltd, Witney, UK). Data were measured as mmol/L and are shown as mean±SEM from n mice. GraphPad® Prism 5.04 (GraphPad Software, La Jolla, CA, USA) was used to generate the diagrams. Statistical differences were tested using unpaired Student's t test and was considered significant for $p<0.05$ (*), $p<0.01$ () and $p<0.001$ (*).

Example 4—[$^{18}$F]Fluoride Drying

No-carrier-added [$^{18}$F]fluoride was produced from [$^{18}$O]H$_2$O ($^{18}$O(p,n)$^{18}$F) on an ACSI TR-19/9 cyclotron and provided as an aqueous solution (1-2 GBq). [$^{18}$F]fluoride was captured on a strong anion-exchange extraction cartridge (Waters, Sep-Pak Accell Plus QMA Plus Light) after priming with aqueous K$_2$CO$_3$ (0.5 M, 8 mL) and water (10 mL). [$^{18}$F]fluoride was eluted with 1.5 mL of a solution (14% H$_2$O, 86% CH$_3$CN) containing K222 (26.6 mM) and K$_2$CO$_3$ (13.3 mM). The [$^{18}$F]fluoride was dried by azeotropic distillation at 90-100° C. under N$_2$ flow using 3 sequential 1 mL additions of anhydrous CH$_3$CN.

Example 5—Preparation of Nitrile Intermediates

In a typical labeling procedure, to the residue of dried [$^{18}$F]KF/K222 was added 0.01 g (0.044 mmol) of either (2S)-(+)-glycidyl tosylate or (2R)-(−)-glycidyl tosylate as a solution in anhydrous CH$_3$CN (0.4 mL). The vial was sealed tightly and heated for 25 min at 95° C. The radioproduct is volatile (epifluorohydrin b.p. 85° C.). RadioTLC of this intermediate is uninformative due to its volatility. After allowing the vial to cool to room temperature, an aqueous solution (50 µL, 3.0 M) of KCN was directly added, the vial resealed, and the mixture briefly vortexed and heated at 95° C. for 15-20 min. RadioTLC of nitrile intermediates on silica gel showed incorporations of 85±9% (M±SD, n=7), Rf=0.4, 1:2 hexanes:EtOAc; however, radioTLC at this stage is not quantitative owing to the possibility of residual [$^{18}$F]epifluorohydrin evaporating prior to plate reading. The reaction mixture containing the nitrile intermediate was filtered through a neutral alumina cartridge (Waters Sep-Pak Alumina N Plus Light Cartridge), the cartridge flushed with THF, and the combined eluates (containing CH$_3$CN, H$_2$O, and THF) condensed to a residue under $N_2$ stream at room temperature. The residue was resuspended in water and the product was purified by HPLC on a C18 column eluting with isocratic water. The chemical identities of the nitrile intermediates were confirmed by co-elution with non-UV active racemic reference standard Example 6—Preparation of (3S)- or (3R)-4-[$^{18}$F] fluoro-3-hydroxybutyric acid, (S)[$^{18}$F]FBHB and (R)[$^{18}$F]FBHB The aqueous solution of HPLC purified nitrile was concentrated to a volume of ≈0.5 mL by rotary evaporation under moderate heating (bath temp≈60° C.) and transferred to a lo-bind snap cap microcentrifuge tube. *E. coli*-derived nitrilase enzyme (1 mg) was added to the aqueous solution along with a small volume of TRIS buffer (10-20 μL of 10 mM, pH 9) to achieve a solution pH of 9. The enzymatic reaction was placed on a thermoshaker at 30° C., 750 rpm for 60 min. Conversion was monitored by radioTLC (silica gel, carboxylic acid (S)[$^{18}$F]FBHB/(R)[$^{18}$F]FBHB Rf=0.1-0.2, EtOAc+1% AcOH). The final product acid (S)[$^{18}$F]FBHB/(R)[$^{18}$F]FBHB was purified and prepared as a concentrated injectable solution using a strong anion-exchange cartridge (Waters, Sep-Pak Accell Plus QMA Plus Light Cartridge). After loading the enzyme reaction mixture onto the QMA, the cartridge was washed sequentially with EtOH (3 mL) and water (3 mL), and eluted with NaOAc buffer (0.25M, pH 5.5) as an injectable solution. Radiochemical purity of the final products were assessed by a Shimadzu UFLC using a Kinetex 2.6 μm F5 100 Å LC column 150×4.6 mm (Phenomenex), gradient elution, 0-30% $CH_3CN$ in $H_2O$, 20 min. Molar activity could not be determined due to a lack of UV absorbance for the cold standard acid. Nitrilase activity showed stereopreference for conversion of R nitrile. Isolated RCY (enzyme reaction) 10% (compound (S)[$^{18}$F]FBHB), 35% (compound (R)[$^{18}$F]FBHB), radiopurity >98%. Total RCY from cyclotron-generated $^{18}$F to isolated injection solution: 13% ((R)-[$^{18}$F]FBHB), 1.3% ((S)[$^{18}$F]FBHB). Total synthesis time from cyclotron-generated $^{18}$F to purified, injectable solution: 4 h.

Example 7—Results

Discussed below are results obtained in connection with the experiments of Examples 1-6.

pared to muscle tissue. FIGS. 3B and 3C are graphs demonstrating uptake of (R)[$^{18}$F]FBHB in subcutaneous tumors of the breast cancer cell lines MCF-7 (estrogen receptor positive) (FIG. 3B) and MDA-MB231 (triple negative model) (FIG. 3C).

FIG. 4A shows dynamic PET scans over 30 minutes of normal BALB/c mice showing the anticipated renal clearance pathway for (S)[$^{18}$F]FBHB and (R)[$^{18}$F]FBHB (upper panel), and moderate heart and brain uptake and retention for both radiopharmaceuticals (lower panel), with brain retention highest for the S isomer (lower panel). FIGS. 4B and 4C are graphs demonstrating moderate heart (FIG. 4B) and brain (FIG. 4C) uptake and retention for both (S)[$^{18}$F]FBHB and (R)[$^{18}$F]FBHB.

FIG. 5 shows transaxial PET scans after administration of (R)[$^{18}$F]FBHB of the heart region of a wild type mouse with transverse aortic constriction-induced heart failure (left), and a mouse with induced heart failure and a knock out for the gene OXTC1 which codes for the ketone body metabolizing enzyme 3-oxoacid CoA transferase 1 (right).

FIGS. 6A-C are graphs showing the dynamic uptake of (R)[$^{18}$F]FBHB expressed as SUV ratio versus time and indicating that a 24 hour fast of MCF7 tumor-bearing mice leads to increased heart (FIG. 6B) and brain (FIG. 6A) uptake of (R)[$^{18}$F]FBHB as well as better tumor retention (FIG. 6C).

FIG. 7 is a graph showing the dynamic uptake of (R)[$^{18}$F]FBHB expressed as SUV ratio versus time and indicating that tumor retention of (R)[$^{18}$F]FBHB in mice bearing triple negative (MDA-MB231) breast cancer tumors was higher in mice fed a glucose-free, fructose-based diet.

Figure 8A:
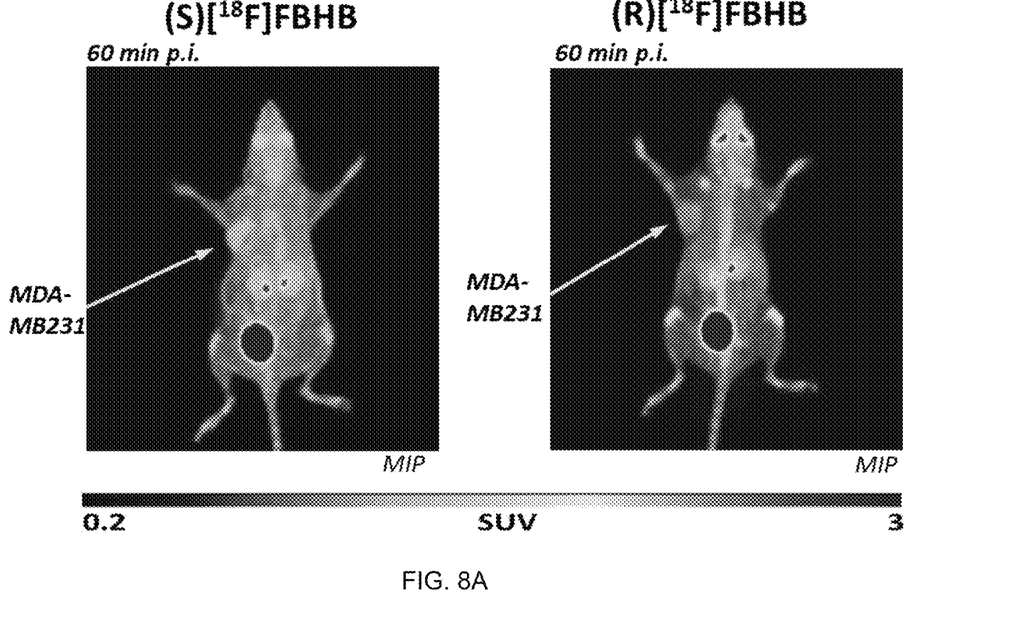
FIG. 8A shows a comparison of PET images for the uptake of (S)[$^{18}$F]FBHB versus (R)[$^{18}$F]FBHB in a mouse model having a subcutaneous MDA-MB-231 xenograft breast cancer tumor.
Figure 8B:
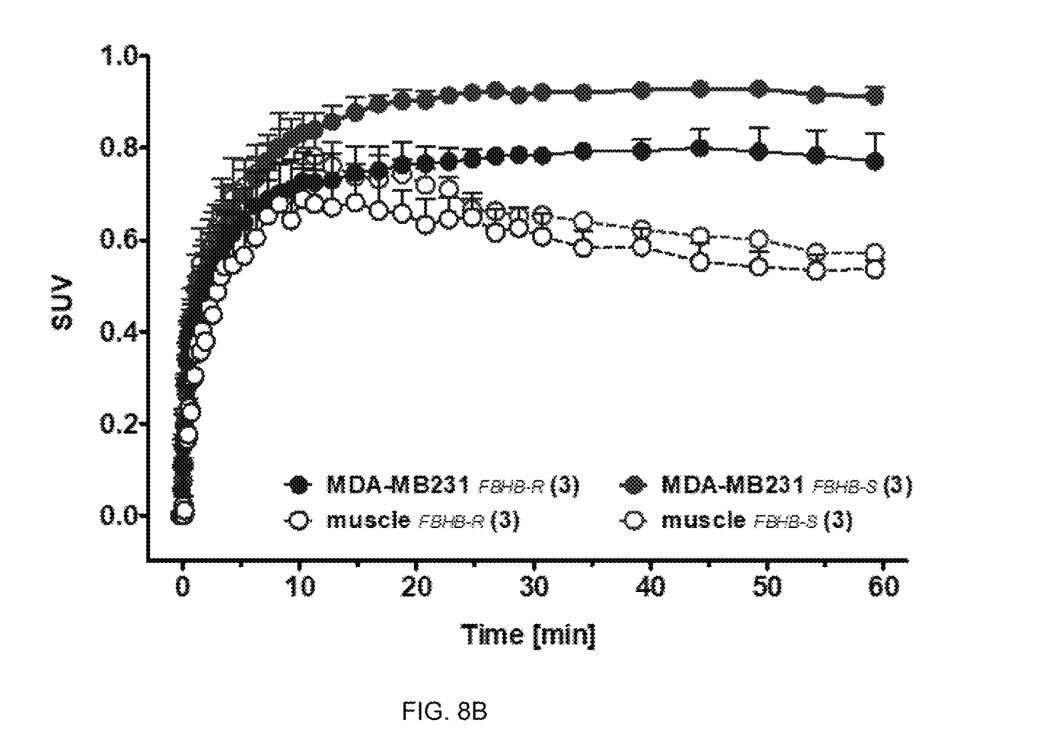
FIG. 8B is a graphical representation comparing tumor uptake with muscle uptake for each isomer, where the S isomer displayed higher uptake. MIP, maximum intensity projection.

FIG. 8A shows a comparison of PET images for the uptake of (S)[$^{18}$F]FBHB versus (R)[$^{18}$F]FBHB in a mouse model having a subcutaneous MDA-MB-231 xenograft breast cancer tumor. FIG. 8B is a graphical representation comparing tumor uptake with muscle uptake for each isomer, where the S isomer displayed higher uptake.

Figure 9A:
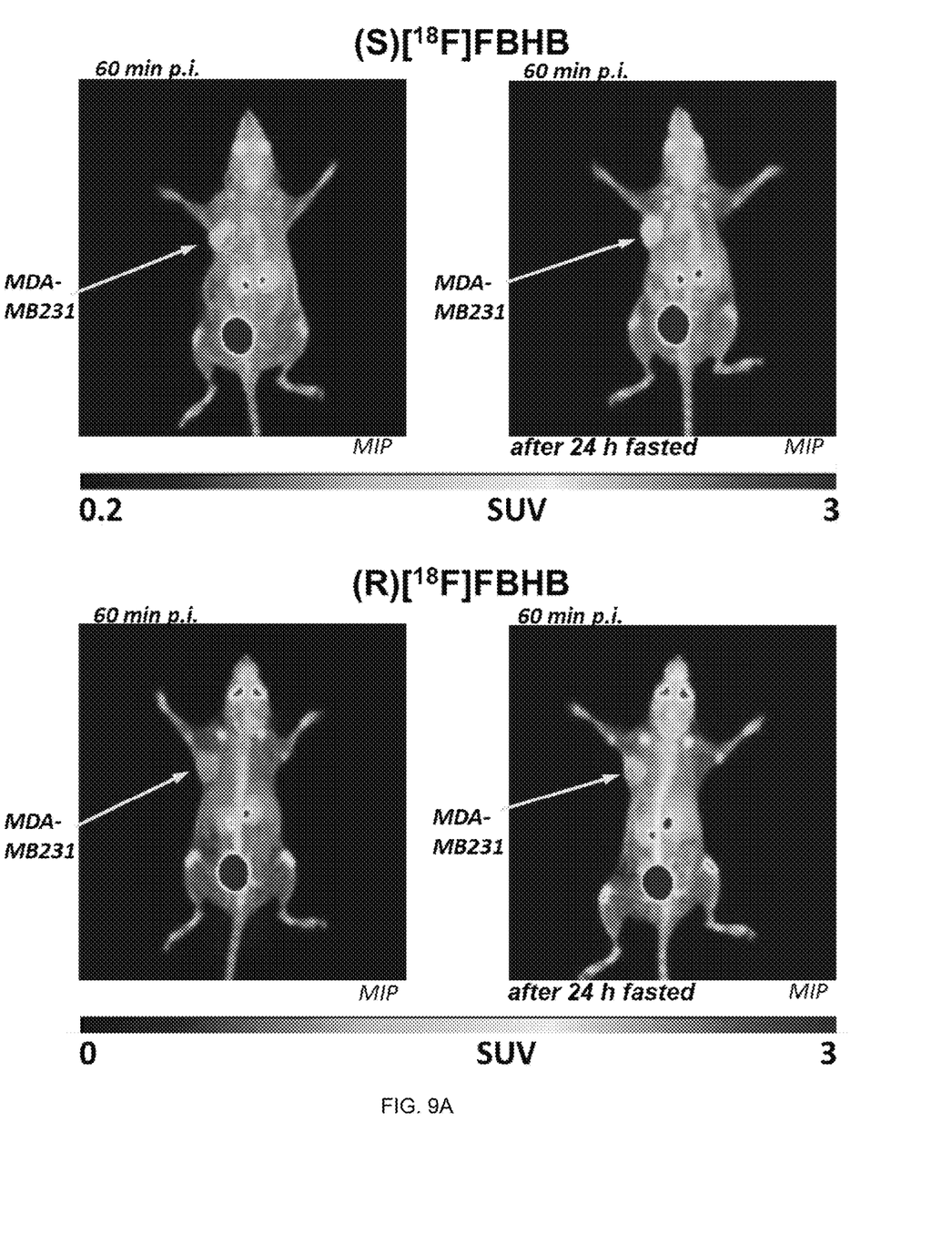
FIG. 9A shows representative PET images of MDA-MB-231 tumor-bearing mice at 60 minutes post injection of (S)[$^{18}$F]FBHB or (R)[$^{18}$F]FBHB in a fed state (left) or after a 24 hour fast (right). MIP, maximum intensity projection.
Figure 9B:
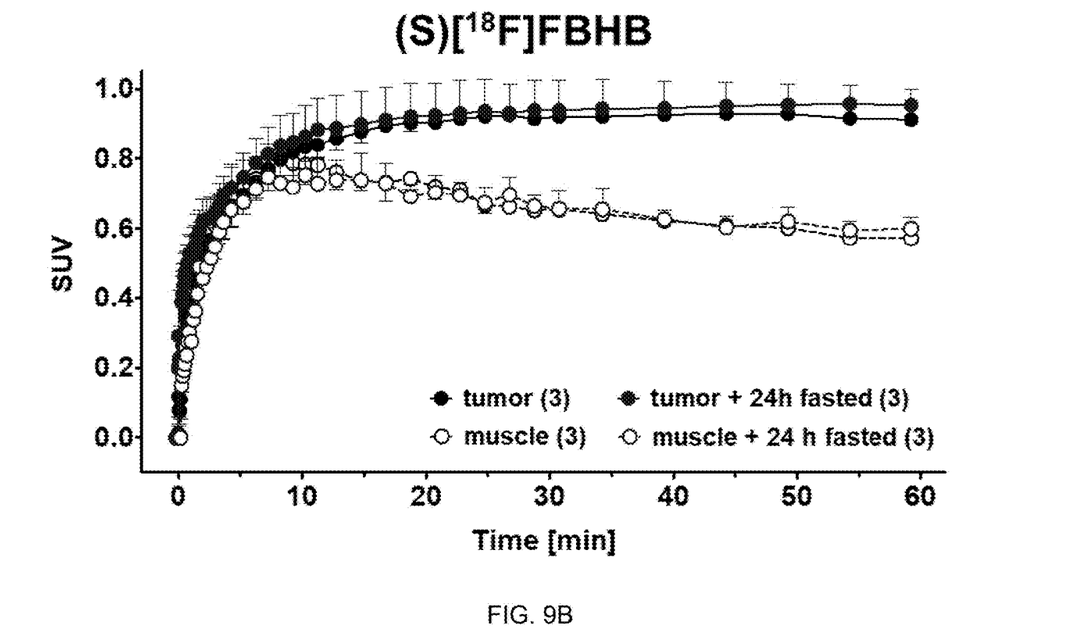
FIGS. 9B-C show time activity curves for MDA-MB-231 tumor and muscle uptake. A statistically significant increase in uptake of (R)[$^{18}$F]FBHB was observed for the fasted condition. Semi-quantitative data are shown as mean±SEM from three experiments per condition. MIP, maximum intensity projection.
Figure 9C:
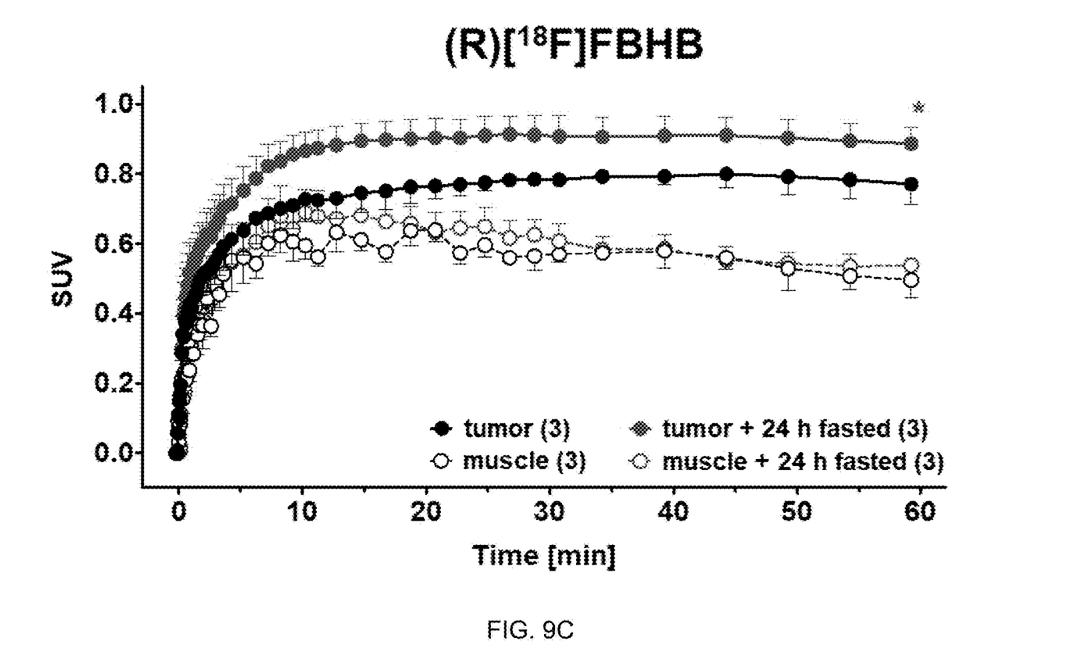

FIG. 9A shows PET images of MDA-MB-231 tumor-bearing mice at 60 minutes post injection of (S)[$^{18}$F]FBHB or (R)[$^{18}$F]FBHB in a fed state (left) or after a 24 hour fast (right). FIGS. 9B-C show time activity curves for MDA-MB-231 tumor and muscle uptake. A statistically significant increase in uptake of (R)[$^{18}$F]FBHB was observed for the fasted condition.

Table 1 summarizes the fasting-induced changes in radiotracer retention for (S)[$^{18}$F]FBHB and (R)[$^{18}$F]FBHB in selected organs. SUV mean, 60 min (n=3), *=p<0.05.

TABLE 1

|  | (S)[$^{18}$F]FBHB | (S)[$^{18}$F]FBHB 24 h fasted | (R)[$^{18}$F]FBHB | (R)[$^{18}$F]FBHB 24 h fasted |
|---|---|---|---|---|
| tumor | 0.91 ± 0.02 | 0.95 ± 0.04 | 0.77 ± 0.06 | 0.89 ± 0.05 * |
| muscle | 0.57 ± 0.01 | 0.60 ± 0.03 | 0.50 ± 0.05 | 0.54 ± 0.02 |
| heart | 0.96 ± 0.01 | 1.05 ± 0.02 * | 0.84 ± 0.09 | 0.95 ± 0.03 $^{n.s.}$ |
| brain | 1.08 ± 0.02 | 1.17 ± 0.02 * | 0.91 ± 0.07 | 1.02 ± 0.05 $^{n.s.}$ |
| joint | 1.10 ± 0.08 | 1.07 ± 0.08 | 1.30 ± 0.10 | 1.58 ± 0.02 $^{p=0.0501}$ |
| spine | 1.10 ± 0.07 | 1.13 ± 0.04 | 1.39 ± 0.03 | 1.56 ± 0.03 * |
| liver | 0.74 ± 0.01 | 0.80 ± 0.02 * | 0.66 ± 0.08 | 0.74 ± 0.02 $^{n.s.}$ |
| kidneys | 1.44 ± 0.05 | 1.38 ± 0.16 | 1.96 ± 0.17 | 2.36 ± 0.25 $^{n.s.}$ |
| Harderian glands | 1.10 ± 0.01 | 1.15 ± 0.02 |  | 1.56 ± 0.13 | 1.39 ± 0.11 $^{n.s.}$ |

Figure 3A:
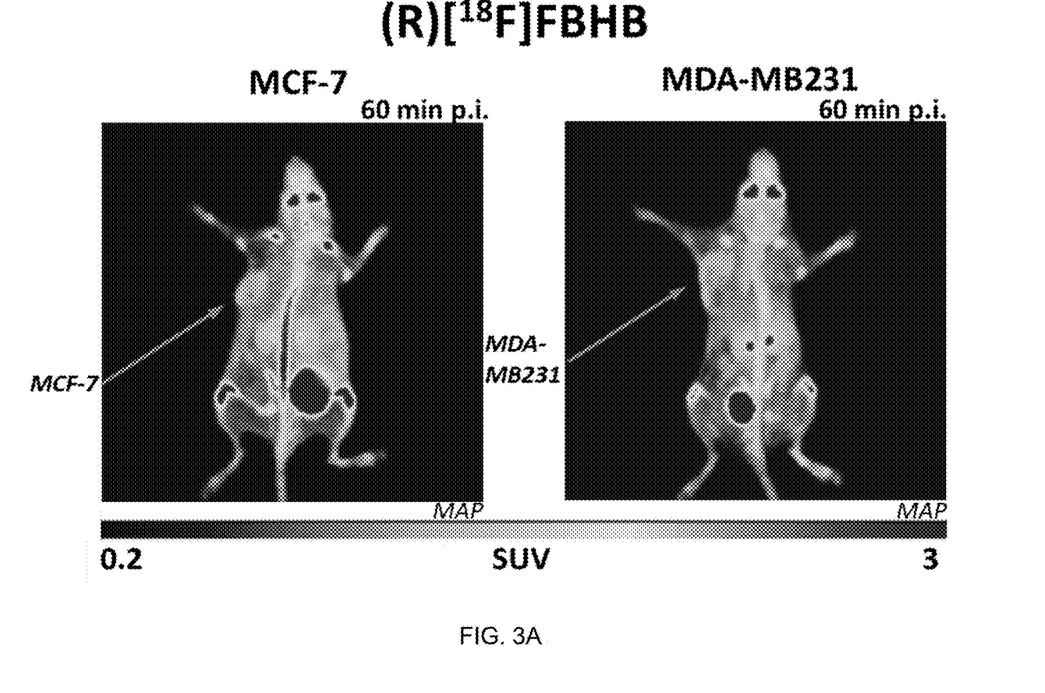
FIG. 3A shows positron emission tomography ("PET") images demonstrating uptake of (R)[$^{18}$F]FBHB in subcutaneous tumors of the breast cancer cell lines MCF-7 (estrogen receptor positive) and MDA-MB231 (triple negative model). MAP, maximum a priori.
Figure 3B:
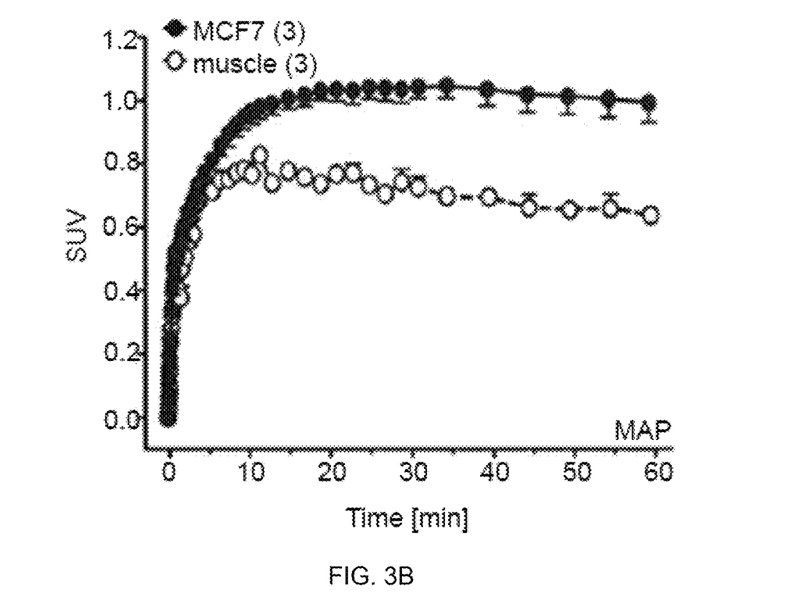
FIGS. 3B and 3C are graphs demonstrating uptake of (R)[$^{18}$F]FBHB in subcutaneous tumors of the breast cancer cell lines MCF-7 (estrogen receptor positive) (FIG. 3B) and MDA-MB231 (triple negative model) (FIG. 3C). MAP, maximum a priori.
Figure 3C:
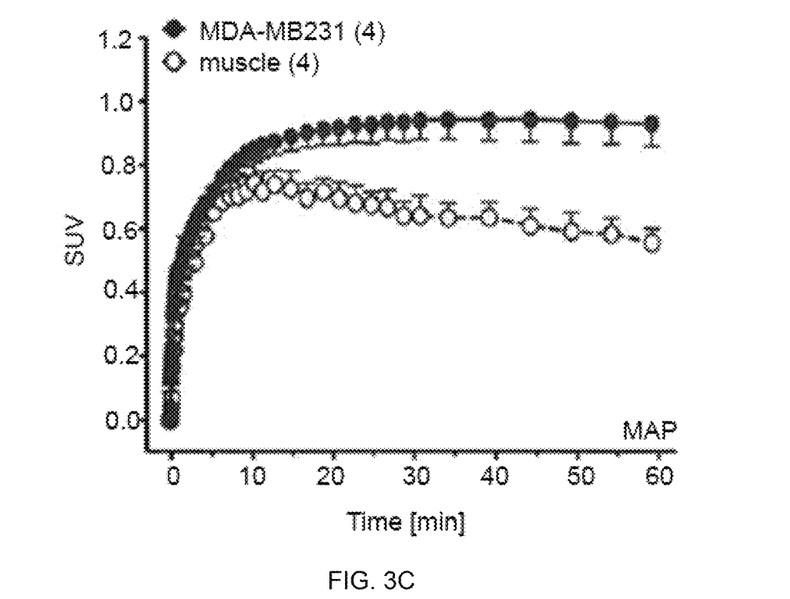

FIG. 3A shows positron emission tomography ("PET") images demonstrating uptake of (R)[$^{18}$F]FBHB in subcutaneous tumors of the breast cancer cell lines MCF-7 (estrogen receptor positive) and MDA-MB231 (triple negative model), showing higher retention in tumor tissue as com-

As will be apparent to those skilled in the art, various modifications, adaptations and variations of the foregoing specific disclosure can be made without departing from the scope of the invention claimed herein.

What is claimed is:

1. A compound of:
   (a) (S)-[$^{18}$F]γ-fluoro-β-hydroxybutyric acid having the absolute stereochemistry of formula (I):

(I)

wherein the hydroxylated carbon at position 3 has (S) stereochemistry;
   or a pharmaceutically acceptable salt, solvate, or hydrate thereof; or
   (b) (R)-[$^{18}$F]γ-fluoro-β-hydroxybutyric acid having the absolute stereochemistry of formula (II):

(II)

wherein the hydroxylated carbon at position 3 has (R) stereochemistry;
   or a pharmaceutically acceptable salt, solvate, or hydrate thereof.

2. A composition comprising the compound of claim 1 and a pharmaceutically acceptable carrier.

3. A method for diagnosing, staging, or treating a disorder in a subject comprising:
   administering a radiopharmaceutical to the subject; and
   imaging an organ or tissue of interest using positron emission tomography;
   wherein the radiopharmaceutical comprises the compound of (S)-[$^{18}$F]γ-fluoro-β-hydroxybutyric acid having the absolute stereochemistry of formula (I)

(I)

wherein the hydroxylated carbon at position 3 has (S) stereochemistry, (R)-[$^{18}$ F]γ-fluoro-β-hydroxybutyric acid having the absolute stereochemistry of formula (II)

(II)

wherein the hydroxylated carbon at position 3 has (R) stereochemistry, or a pharmaceutically acceptable salt, solvate, hydrate, or composition thereof, and is capable of being retained within the organ or tissue sufficient to emit positrons for detection by positron emission tomography.

4. The method of claim 3 wherein the disorder is selected from Alzheimer's disease, epilepsy, cancer, cardiovascular disease, or diabetes.

5. The method of claim 4, wherein the cardiovascular disease is heart failure.

6. The method of claim 4, wherein the cancer is breast cancer.

7. The method of claim 3, wherein the organ or tissue is selected from the brain, breast, heart, eye, or a tumor.

8. A method for monitoring a disorder in a subject comprising:
   administering a radiopharmaceutical to a subject undergoing medical treatment for the disorder;
   imaging an organ or tissue of interest using positron emission tomography; and
   comparing the quantity or distribution of the radiopharmaceutical present in the subject with a control quantity or distribution indicative of the effectiveness of the medical treatment;
   wherein the radiopharmaceutical comprises the compound of (S)-[$^{18}$F]γ-fluoro-β-hydroxybutyric acid having the absolute stereochemistry of formula (I) wherein the hydroxylated carbon at position 3 has (S) stereochemistry, (R)-[$^{18}$ F]γ-fluoro-β-hydroxybutyric acid having the absolute stereochemistry of formula (II) wherein the hydroxylated carbon at position 3 has (R) stereochemistry, or a pharmaceutically acceptable salt, solvate, hydrate, or composition thereof, and is capable of being retained within the organ or tissue sufficient to emit positrons for detection by positron emission tomography.

9. The method of claim 8, wherein the disorder is selected from Alzheimer's disease, epilepsy, cancer, cardiovascular disease, or diabetes.

10. The method of claim 9, wherein the cardiovascular disease is heart failure.

11. The method of claim 9, wherein the cancer is breast cancer.

12. The method of claim 8, wherein the organ or tissue is selected from the brain, breast, heart, eye, or a tumor.

13. The method of claim 8, wherein the medical treatment is ketogenic diet therapy.

* * * * *